(12) United States Patent
Lockhart et al.

(10) Patent No.: US 9,242,061 B2
(45) Date of Patent: Jan. 26, 2016

(54) FLUID COUPLING CONDUIT WITH EXHAUST GAS NOISE REDUCTION

(75) Inventors: Harold Allen Lockhart, Eindhoven (NL); Duon Alex Truong, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 265 days.

(21) Appl. No.: 13/879,086

(22) PCT Filed: Oct. 17, 2011

(86) PCT No.: PCT/IB2011/054591
§ 371 (c)(1),
(2), (4) Date: Apr. 12, 2013

(87) PCT Pub. No.: WO2012/052906
PCT Pub. Date: Apr. 26, 2012

(65) Prior Publication Data
US 2013/0199538 A1     Aug. 8, 2013

Related U.S. Application Data

(60) Provisional application No. 61/405,804, filed on Oct. 22, 2010.

(51) Int. Cl.
*A61M 16/06*     (2006.01)
*A61M 16/08*     (2006.01)
*A61M 16/00*     (2006.01)

(52) U.S. Cl.
CPC ............ *A61M 16/06* (2013.01); *A61M 16/0057* (2013.01); *A61M 16/0633* (2014.02); *A61M 16/0816* (2013.01); *A61M 16/0875* (2013.01); *A61M 2205/42* (2013.01)

(58) Field of Classification Search
CPC ............ A61M 16/00; A61M 16/0057; A61M 16/0066; A61M 16/0069; A61M 16/009; A61M 16/04; A61M 16/0488; A61M 16/0493; A61M 16/06; A61M 16/0605; A61M 16/0611; A61M 16/0616; A61M 16/0622; A61M 16/0633; A61M 16/0638; A61M 16/0666; A61M 16/0683; A61M 16/08; A61M 16/0816; A61M 16/0825; A61M 16/0841; A61M 16/085; A61M 16/0858; A61M 16/0875; A61M 16/1065; A61M 16/109; A61M 16/1095; A61M 16/20; A61M 16/208; A61M 35/00; A61M 39/10; A62B 18/00; A62B 18/02; A62B 18/08; A62B 18/10; A62B 7/00; A62B 9/02; A62B 9/04; F16K 27/00
USPC ............ 128/200.24, 200.26, 202.27, 204.18, 128/205.11, 205.24, 205.25, 206.15, 128/206.21, 206.24, 206.27, 206.28, 128/207.11, 207.12, 207.13, 207.18, 912
See application file for complete search history.

(56) References Cited

U.S. PATENT DOCUMENTS

| 6,615,830 | B1 | 9/2003 | Serowski et al. | |
|---|---|---|---|---|
| 2003/0094177 | A1* | 5/2003 | Smith et al. | 128/204.18 |
| 2004/0025881 | A1* | 2/2004 | Gunaratnam et al. | 128/206.15 |
| 2005/0172969 | A1 | 8/2005 | Ging | |
| 2008/0047561 | A1* | 2/2008 | Fu et al. | 128/207.12 |
| 2008/0276937 | A1* | 11/2008 | Davidson et al. | 128/204.18 |
| 2009/0032026 | A1* | 2/2009 | Price et al. | 128/207.11 |
| 2009/0044808 | A1* | 2/2009 | Guney et al. | 128/206.24 |
| 2009/0241965 | A1 | 10/2009 | Sather | |
| 2011/0240030 | A1* | 10/2011 | Ho et al. | 128/206.21 |
| 2012/0132209 | A1* | 5/2012 | Rummery et al. | 128/205.25 |

FOREIGN PATENT DOCUMENTS

| CN | CN 1688358 A | 10/2005 |
|---|---|---|
| CN | CN 101098727 A | 1/2008 |
| EP | 2027880 A1 | 2/2009 |
| EP | EP2281597 A1 | 2/2011 |
| WO | WO02051486 A1 | 7/2002 |
| WO | WO2005063326 A1 | 7/2005 |
| WO | WO2007012140 A1 | 2/2007 |
| WO | WO2010067237 A2 | 6/2010 |

OTHER PUBLICATIONS

Pettenski, T.A., "Evaluation of Multi-Layer Mask Concept for Respo 21", Dec. 1991.

\* cited by examiner

*Primary Examiner* — Annette Dixon
(74) *Attorney, Agent, or Firm* — Michael W. Haas

(57) ABSTRACT

A fluid coupling conduit (6, 50, 70, 104, 134) includes an inlet end (28, 52, 76, 110, 140) structured to receive a flow of breathing gas, an outlet end (32, 56, 78, 112, 142) fluidly coupled to the inlet end and defining an outlet opening, a central chamber portion (36, 60, 80, 124, 145) positioned between the inlet end and the outlet end, the central chamber portion having an outer wall (38, 62, 82, 116, 146) positioned opposite the outlet opening. The outer wall has a plurality of exhaust gas orifices (40, 64, 84, 118, 148) extending therethrough. A number of sound attenuating structures are disposed in the central chamber portion between the outlet opening and the outer wall. The sound attenuating structures including a plurality of surfaces structured to reflect sound waves associated with exhaust gas flow through the fluid coupling conduit.

14 Claims, 16 Drawing Sheets

FLUID COUPLING CONDUIT WITH EXHAUST GAS NOISE REDUCTION

CROSS-REFERENCE TO RELATED APPLICATIONS

This patent application claims the priority benefit under 35 U.S.C. §371 of international patent application no. PCT/IB2011/054591, filed Oct. 17, 2011, which claims the priority benefit under 35 U.S.C. §119(e) of U.S. Provisional Application No. 61/405,804 filed on Oct. 22, 2010, the contents of which are herein incorporated by reference.

BACKGROUND OF THE INVENTION

1. Field of the Invention

The present invention relates to non-invasive ventilation and pressure support systems that use a patient interface device to deliver a flow of breathing gas to the airway of a patient, and, in particular, to a fluid coupling conduit, such as an elbow conduit, for such a patient interface device that includes a mechanism for reducing noise associated with the exhaust gas flow.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver positive airway pressure (PAP) therapy to treat certain medical disorders, the most notable of which is obstructive sleep apnea (OSA). Known PAP therapies include continuous positive airway pressure (CPAP), wherein a constant positive pressure is provided to the airway of the patient in order to splint open the patient's airway, and variable airway pressure, wherein the pressure provided to the airway of the patient is varied with the patient's respiratory cycle. Such therapies are typically provided to the patient at night while the patient is sleeping.

Non-invasive ventilation and pressure support therapies as just described involve the placement of a patient interface device including a mask component having a soft, flexible cushion on the face of a patient. The mask component may be, without limitation, a nasal mask that covers the patient's nose, a nasal cannula having nasal prongs that are received within the patient's nares, a nasal/oral mask that covers the nose and mouth, or a full face mask that covers the patient's face. Such patient interface devices may also employ other patient contacting components, such as forehead supports, cheek pads and chin pads. The patient interface device is connected to a gas delivery hose and interfaces the ventilator or pressure support device with the airway of the patient, so that a flow of breathing gas can be delivered from the pressure/flow generating device to the airway of the patient. It is known to maintain such devices on the face of a wearer by a headgear having one or more straps adapted to fit over/around the patient's head.

For patient interface devices used in, for example, the treatment of OSA, a key engineering challenge is to balance the exhaust gas flow and the exhaust gas noise. A certain amount of exhaust gas flow is required for all such patient interface devices to properly expel as much $CO_2$ as possible. The amount of exhaust gas flow currently required to expel the proper amount of $CO_2$ also makes the patient interface devices somewhat noisy. This noise could disturb a patient or bed partner, sometimes to the point where he or she will not be able to fall asleep or will be woken up inadvertently.

Most current patient interface devices utilize an elbow conduit for controlling the exhaust gas flow through small orifices. These orifices are molded in such a way to reduce noise as much as possible. Due to orifice complexity, most exhalation/exhaust ports are molded as separate pieces and assembled to form a complete elbow. Currently, no balance has been achieved in maintaining acceptable flow levels and low noise thresholds utilizing small orifices alone. Thus, an important opportunity exists for achieving acceptable flow levels and low noise thresholds.

SUMMARY OF THE INVENTION

Accordingly, it is an object of the present invention to provide a patient interface device that overcomes the shortcomings of conventional patient interface device. This object is achieved according to one embodiment of the present invention by providing a patient interface device that includes a cushion and a frame. The cushion being coupled to the frame. The frame having an orifice in fluid communication with the cushion. The patient interface device further includes a fluid coupling conduit having an inlet end and an outlet end fluidly coupled to the inlet end. The inlet end is structured to receive a flow of breathing gas, and the outlet end is structured to be fluidly coupled to the orifice of the frame to deliver the flow of breathing gas to the cushion. The fluid coupling conduit includes a central chamber portion positioned between the inlet end and the outlet end, the central chamber portion having an outer wall structured to be positioned opposite the orifice of the frame when the outlet end is fluidly coupled to the orifice. The outer wall has a plurality of orifices extending therethrough. The fluid coupling conduit includes a number of sound attenuating structures in the central chamber portion between the outlet end and the outer wall. The number of sound attenuating structures includes a plurality of surfaces structured to reflect sound waves associated with exhaust gas flow through the orific.

In another embodiment, a fluid coupling conduit, such as an elbow conduit, is provided, that includes an inlet end structured to receive a flow of breathing gas, an outlet end fluidly coupled to the inlet end, wherein the outlet end defines an outlet opening, a central chamber portion positioned between the inlet end and the outlet end. The central chamber portion has an outer wall positioned opposite the outlet opening. The outer wall has a plurality of exhaust gas orifices extending therethrough, and a number of sound attenuating structures in the central chamber portion between the outlet opening and the outer wall. The number of sound attenuating structures including a plurality of surfaces structured to reflect sound waves associated with exhaust gas flow through the fluid coupling conduit.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE EXEMPLARY EMBODIMENTS

Figure 1:
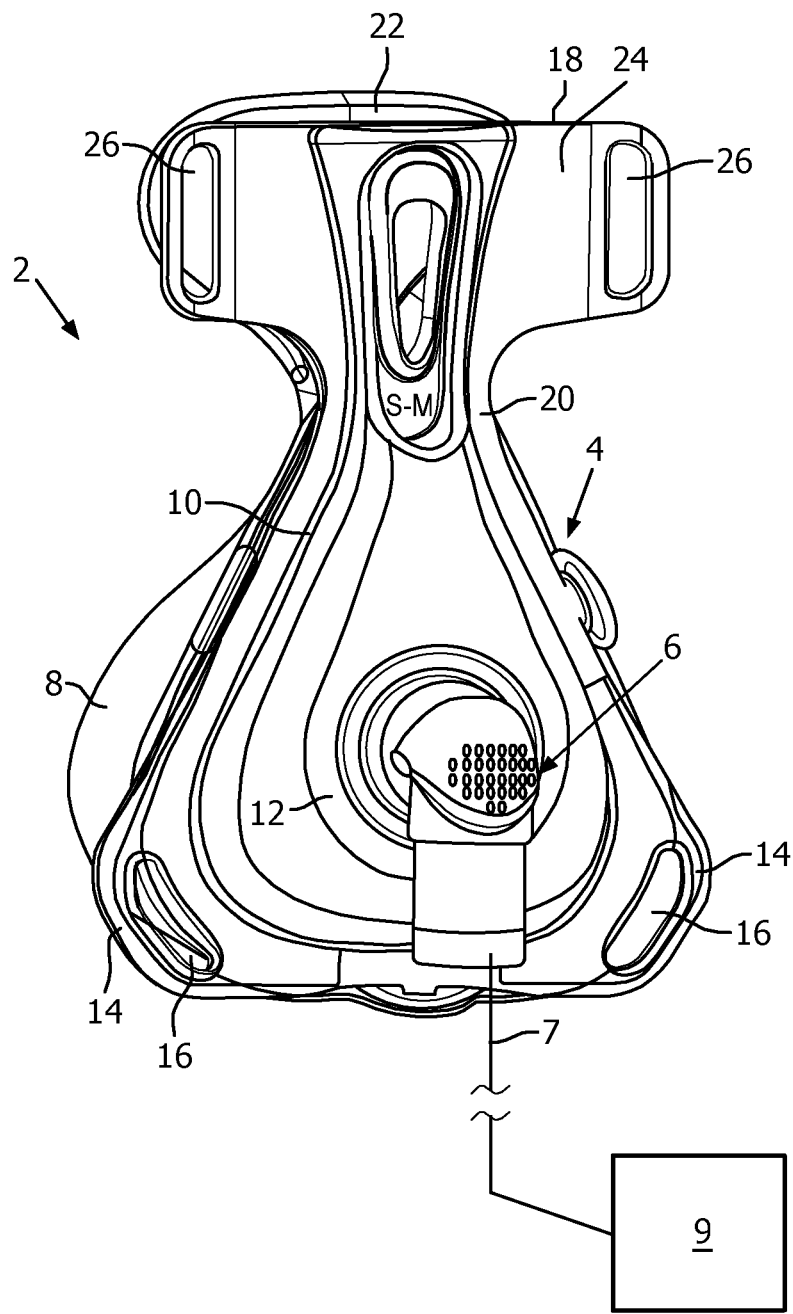
FIG. 1 is a front isometric view of a patient interface device according to one exemplary embodiment of the present invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a front isometric view of a patient interface device 2 that includes a mask 4 that is fluidly coupled to an elbow conduit 6 according to one exemplary embodiment of the present invention. Elbow conduit 6 is structured to be coupled to a suitable hose 7, which, in turn, is coupled to a suitable pressure generating device 9. Pressure generating device includes, without limitation, a constant pressure support device (such as a continuous positive airway pressure device, or CPAP device), a variable pressure device (e.g., BiPAP®, Bi-Flex®, or C-Flex™ devices manufactured and distributed by Philips Respironics of Murrysville, Pa.), an auto-titration pressure support device, a ventilator, or any other device that generates a flow of gas for delivery to a patient. Elbow conduit 6 is described in detail below in connection with FIGS. 2-8.

In the illustrated embodiment, mask 4 is a nasal mask. However, other types of masks, such as a nasal/oral (full face) mask, which facilitate the delivery of a flow of breathing gas to the airway of a patient, may be used as mask 4 while remaining within the scope of the present invention. Mask 4 includes a sealing cushion 8 that is operatively coupled to a frame 10.

In the illustrated embodiment, sealing cushion 8 is defined from a unitary piece of soft, flexible, cushiony, elastomeric material, such as, without limitation, silicone, an appropriately soft thermoplastic elastomer, a closed cell foam, or any combination of such materials. Frame 10 is made of a rigid or semi-rigid material, such as, without limitation, an injection molded thermoplastic or silicone, and includes faceplate portion 12 having an orifice to which elbow conduit 6 is attached.

Frame 10 includes a pair of headgear connecting members 14 disposed on opposites side of a faceplate portion 12 of the frame. In the illustrated exemplary embodiment, wherein each headgear connecting member 14 includes a loop 16 that is structured to receive a respective lower headgear strap of a headgear assembly (not shown) for securing patient interface device 2 to the head of the patient. It is to be understood that other configurations for the headgear connecting member are contemplated by the present invention, such as snaps, slots, hooks, and receptacles.

Frame 10 further includes a forehead support 18 attached to an extension member 20 extending from faceplate portion 12. Forehead support 18 includes a forehead cushion 22 that is coupled to support frame 24. Forehead cushion 22 is made of a soft, flexible, elastomeric material, such as, without limitation, silicone rubber, an appropriately soft thermoplastic elastomer, or any combination of such materials, and, in the exemplary embodiment, is over-molded onto support frame 24. Forehead support 18 is structured to provide additional support for patient interface device 2 by engaging the forehead of the patient. It is to be understood that forehead support 18 and extension member 20 are optional and can be omitted entirely. In addition, numerous other configurations for forehead support 18 and/or extension member 20 are contemplated by the present invention. For example, extension member 20 can include an adjustment mechanism that enables forehead support 18 to move relatively to the frame so that the user can select the proper position for forehead support 18 based on their personal preferences.

In the illustrated embodiment, support frame 24 includes headgear connecting members 26 provided at opposite ends thereof. In this embodiment, headgear connecting members 26 are in the form of a loop structured to receive a respective upper headgear strap of a headgear assembly (not shown) for securing patient interface device 2 to the head of the patient. It is to be understood that other configurations for the headgear connecting member are contemplated by the present invention, such as snaps, slots, hooks, and receptacles.

Figure 2:
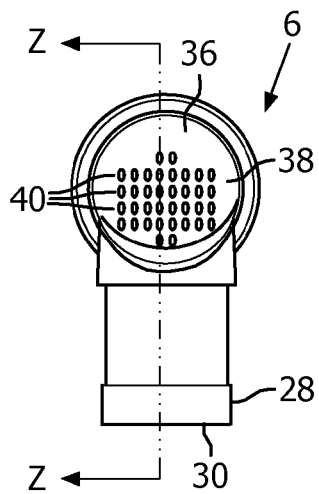
FIG. 2 is a front elevational view.
Figure 3:
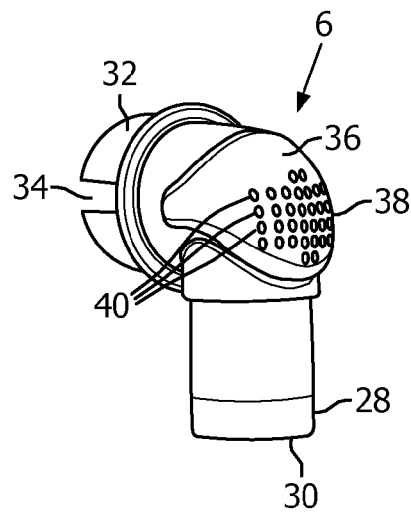
FIG. 3 is a front isometric view.
Figure 4:
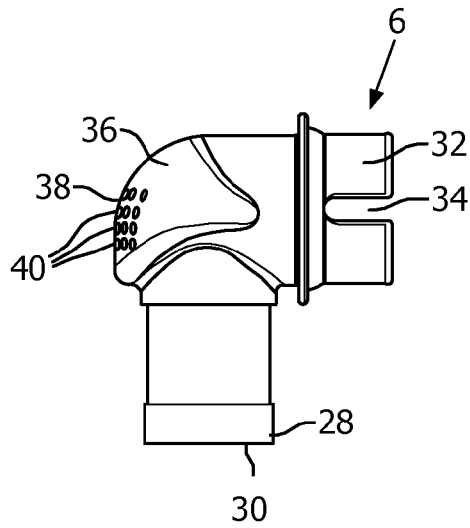
FIG. 4 is a side elevational view.
Figure 5:
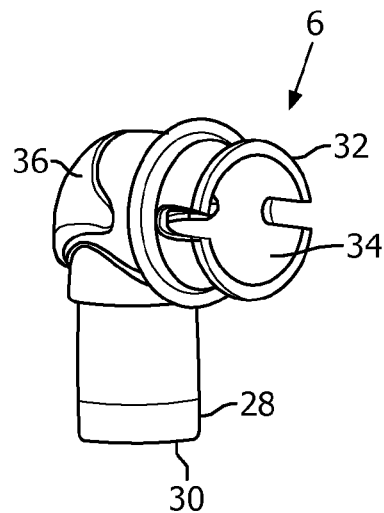
FIG. 5 is a rear isometric view.
Figure 6:
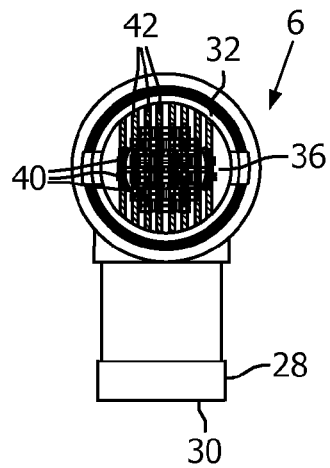
FIG. 6 is a rear elevational view of an elbow conduit according to one embodiment of the invention.

FIG. 2 is a front elevational view, FIG. 3 is a front isometric view, FIG. 4 is a side elevational view, FIG. 5 is a front isometric view, and FIG. 6 is a front elevational view of elbow conduit 6 shown in FIG. 1. In addition, FIGS. 7 and 8 are cross-sectional views of elbow conduit 6 taken along lines Z-Z of FIG. 2.

Referring to FIGS. 2-8, elbow conduit 6 includes an inlet end 28 having an inlet opening 30 structured to be connected to hose 7 connected to pressure generating device 9. Elbow conduit 6 also includes an outlet end 32 having an outlet opening 34 that is in fluid communication with inlet end 28 and inlet opening 30. Outlet end 32 is structured to be removeably and sealingly coupled to faceplate portion 12 of frame 10. In the exemplary embodiment, elbow conduit 6 is integrally molded as a single part from a rigid or semi-rigid material such as, without limitation, a plastic material.

Elbow conduit 6 also includes a central chamber portion 36 (forming the bend of the elbow) between inlet end 28 and outlet end 32. Outer wall 38 of central chamber portion 36 positioned directly opposite outlet opening 34 includes a plurality of integrally molded exhaust gas slots/orifices 40 extending therethrough that allow for the proper dissipation of $CO_2$ to atmosphere as the patient exhales into mask 4. In the illustrated exemplary embodiment, exhaust gas slots/orifices 40 are oval-shaped. However, other shapes are contemplated, such as circular, rectangular, square, etc. In addition, exhaust gas slots/orifices 40 act as sound wave diffractors on the exhaust gas flow in order to reduce the noise caused by the exhaust gas flow. In one particular, non-limiting exemplary embodiment, the diameter of each of the oval-shaped exhaust gas slots/orifices 40 is 0.020 inches and the length of each of the oval-shaped exhaust gas slots/orifices 40 is 0.042 inches.

Figure 7:
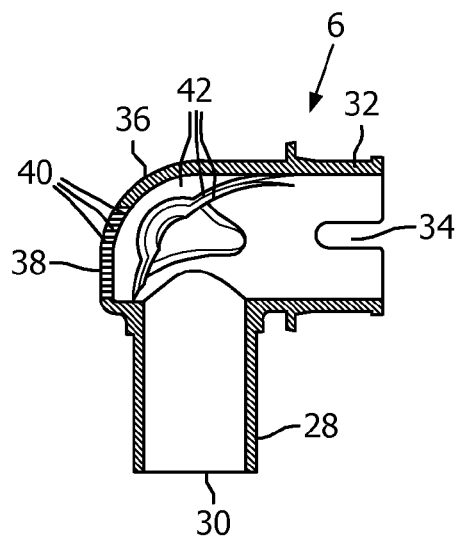
FIGS. 7 and 8 are cross-sectional views of the elbow conduit of FIGS. 2-6 taken along lines Z-Z of FIG. 2.
Figure 8:
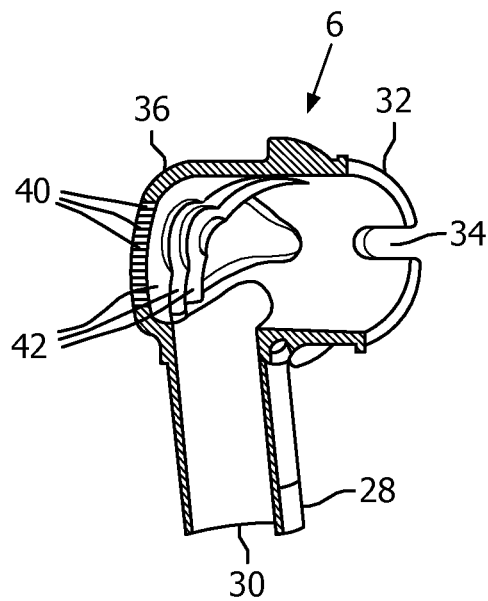
Figure 9:
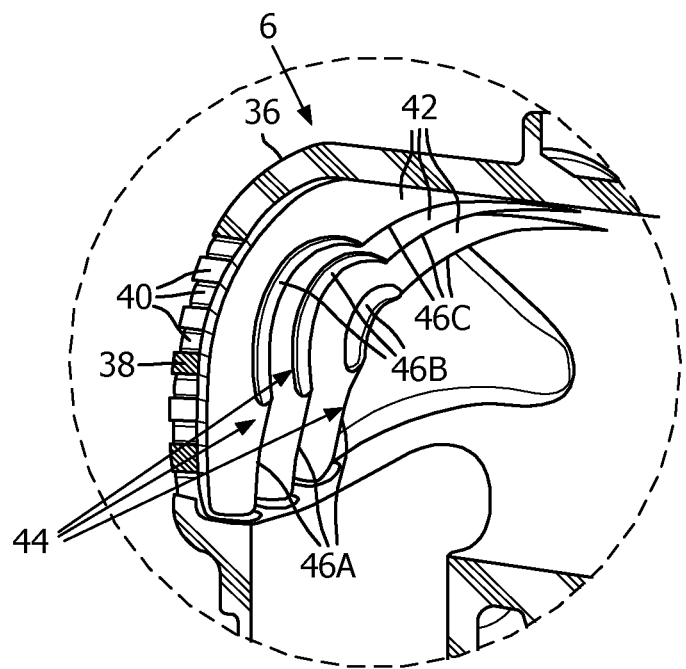
FIG. 9 is a focused view of a selected portion of FIG. 8.

In addition, referring to FIGS. 6-8, central chamber portion 36 includes a plurality of partition members 42. Each partition member 42 is coupled to and extends from the interior surface of outer wall 38 of central chamber portion 36. Furthermore, each partition member 42 includes a leading edge region 44 having a plurality of arc-shaped portions 46 (see FIG. 9). In the illustrated embodiment, leading edge region 44 of each partition member 42 includes three arc-shaped portions 46A, 46B, 46C. Arc-shaped portion 46B is configured as a parabolic notched region located between co-linear arc-shaped portions 46A, 46C. The multi-arced geometry of partition members 42 cause them to act as sound wave reflectors on the exhaust gas flow passing through mask 4. This causes the sound waves associated with the exhaust gas flow to be reflected in multiple directions by the partition members 42 (in particular by the arc-shaped portions 46), resulting in a degree of noise cancellation and, thus, noise reduction as exhaust gasses are passed through elbow conduit 6 to the ambient atmosphere.

It can be appreciated that elbow conduit 6 diverts the exhaust gas flow in such a manner to reduce the sound pressure wave prior to exiting the elbow conduit, thereby reducing noise all the while maintaining the exhaust gas flow, i.e., not imposing a significant restriction on the exhaust gas flow. In particular, exhaust gas slots/orifices 40 and partition members 42 combine to provide both reflection and diffraction of the exhaust gas flow as it passes through elbow conduit 6, which helps reduce the sound pressure wave enough so that a low noise threshold may be achieved while maintaining acceptable flow levels to adequately expel $CO_2$. In the exemplary embodiment, exhaust gas slots/orifices 40 (act as sound wave diffractors) and partition members 42 (comprising multi-parabolic geometric structures that act as sound wave reflectors) and are integrally molded as part of the interior of central chamber portion 36. The integrally molded internal features just described allow elbow conduit 6 in the exemplary embodiment to be molded as a single part, thus eliminating the need for assembly.

Figure 10:
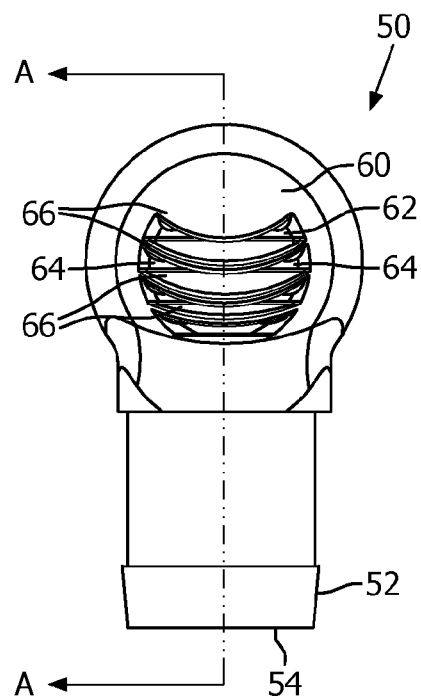
FIG. 10 is a front elevational view.
Figure 11:
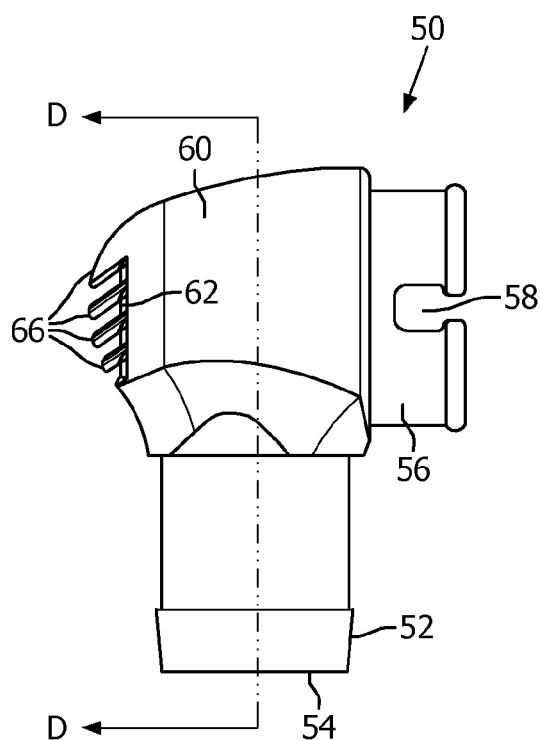
FIG. 11 is a side elevational view.
Figure 12:
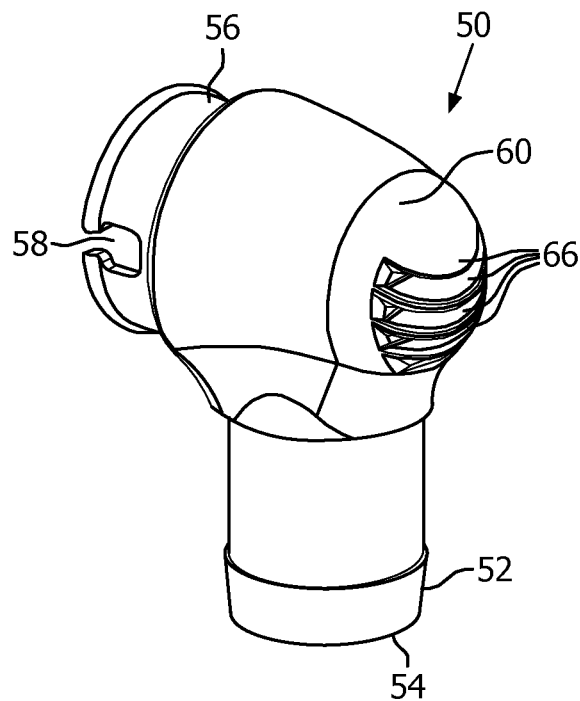
FIG. 12 is a front isometric view.
Figure 13:
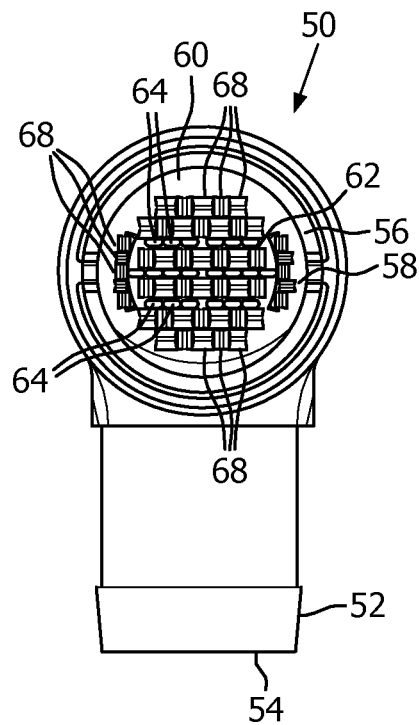
FIG. 13 is a rear elevational view of an elbow conduit according to another exemplary embodiment of the present invention.
Figure 14:
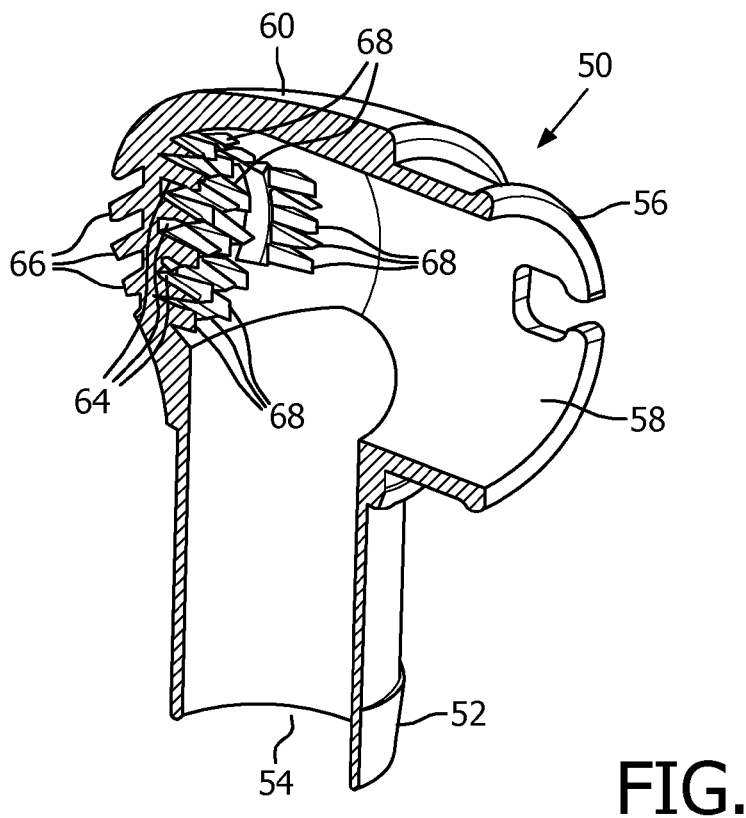
FIG. 14 is a cross-sectional view of the elbow conduit of FIG. 10 taken along lines A-A of FIG. 10.
Figure 15:
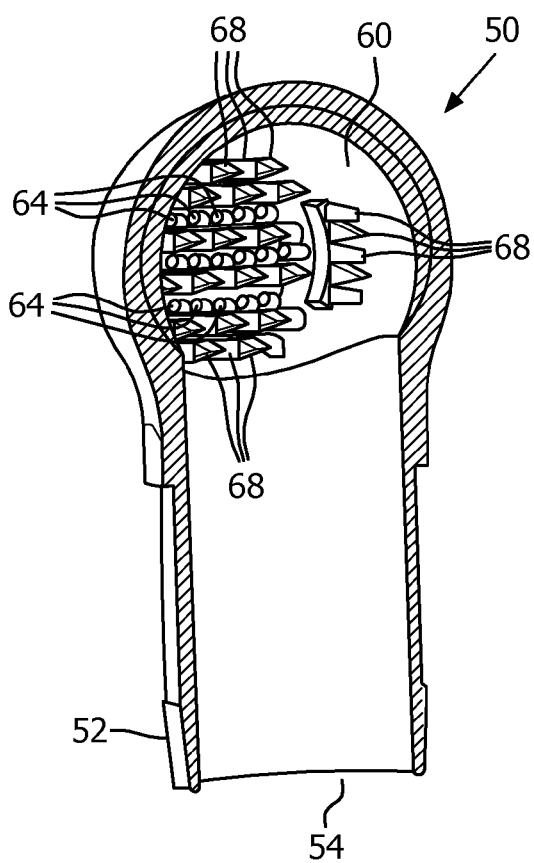
FIG. 15 is a cross-sectional view of the elbow conduit of FIG. 11 taken along lines D-D of FIG. 11.

FIG. 10 is a front elevational view, FIG. 11 is a side elevational view, FIG. 12 is a front isometric view, and FIG. 13 is a rear elevational view of an elbow conduit 50 according to another exemplary embodiment of the present invention. In addition, FIG. 14 is a cross-sectional view of elbow conduit 50 taken along lines A-A of FIG. 10, and FIG. 15 is a cross-sectional view of elbow conduit 50 taken along lines D-D of FIG. 11. Elbow conduit 50 may be used in conjunction with mask 4 shown in FIG. 1 in place of elbow conduit 6, or in conjunction with any other suitable mask structure.

Referring to FIGS. 10-15, elbow conduit 50 includes an inlet end 52 having an inlet opening 54 structured to be connected to a hose connected to a pressure generating device as described elsewhere herein. Elbow conduit 50 also includes an outlet end 56 having an outlet opening 58 that is in fluid communication with inlet end 52 and inlet opening 54. Outlet end 56 is structured to be removeably and sealingly coupled to, for example, faceplate portion 12 of frame 10.

Elbow conduit 50 also includes a central chamber portion 60 (forming the bend of the elbow) between inlet end 52 and outlet end 56. Outer wall 62 of central chamber portion 60 positioned directly opposite outlet opening 58 includes a plurality of integrally molded exhaust gas slots/orifices 64 extending therethrough that allows for the proper dissipation the exhaust gas flow to the ambient atmospheres. In this manner, the $CO_2$ expelled by the patient as the patient exhales into the mask is allowed to exhaust to the ambient atmosphere. In addition, exhaust gas slots/orifices 64 act as sound wave diffractors on the exhaust gas flow in order to reduce the exhaust gas noise caused by the exhaust gas flow.

In one particular, non-limiting exemplary embodiment, the diameter of each of the oval-shaped exhaust gas slots/orifices 64 is 0.020 inches and the length of each of the oval-shaped exhaust gas slots/orifices 64 is 0.042 inches. Furthermore, elbow conduit 50 also includes a plurality of arc shaped deflector members 66 extending outwardly from outer wall 62 at a downward angle with respect to a plane that is parallel to outer wall 62. In one particular, non-limiting embodiment, that downward angle is 60 degrees. Deflector members 66 deflect the diffused exhaust gas flow that passes through exhaust gas slots/orifices 64.

In addition, referring to FIGS. 13-15, central chamber portion 60 includes a plurality of reflecting structures 68. Each reflecting structure 68 is coupled to and extends from an interior surface of central chamber portion 60. Furthermore, each reflecting structure 68 includes a plurality of exterior surfaces that are positioned at an angle with respect to one another. In the illustrated embodiment, each reflecting structure 68 is a triangular prism, although other geometries, such as, without limitation, pyramids and square prisms, are also possible. The multi-angled surface geometry of reflecting structures 68 cause them to act as sound wave reflectors on the exhaust gas flow through elbow conduit 50. This causes the sound waves associated with the exhaust gas flow to be reflected in multiple directions by reflecting structures 68, resulting in some degree of noise cancellation and thus noise reduction as exhaust gasses are passed through elbow conduit 50.

In addition, in the exemplary embodiment, reflecting structures 68 are made of a material having a relatively high sound absorption coefficient to have a greater impact on attenuating the sound pressure wave. For example, and without limitation, reflecting structures 68 may be made of a material such as Silicone, TPE, TPU, or foam, and may have a sound absorption coefficient of between 0.01 and 1.00, which should be greater than that of the rigid or semi-rigid base material. In addition, it should be noted that as a general rule, the absorption coefficient will vary as the wavelength changes. Thus, in one exemplary, non-limiting embodiment, elbow conduit 50 is integrally molded as a single part from two different materials using, for example, a two-shot injection molding process or an insert molding process, wherein inlet end 52, outlet end 56 and central chamber portion 60 may be made from a rigid or semi-rigid material such as, without limitation, a plastic material, and reflecting structures 68 may be made from the higher sound absorption coefficient material just described. Also, during the molding process, the remaining internal surfaces of one or more of inlet end 52, outlet end 56 and central chamber portion 60 may be coated with the higher sound absorption coefficient material to aid in sound absorption.

Furthermore, in the exemplary embodiment, reflecting structures 68 are formed such that they have sufficient structural integrity/rigidity so that higher air pressures of, for example, 40 cmH2O, do not cause reverberation with reflecting structures 68 so as to cause increased sound pressure waves above the low noise thresholds.

Thus, exhaust gas slots/orifices 62 and reflecting structures 68 combine to provide reflection, absorption and diffraction to attenuate the sound pressure wave associated with the exhaust gas flow as it passes through elbow conduit 50, which helps reduce the sound pressure wave enough so that a low noise threshold may be achieved while maintaining acceptable flow levels to adequately expel $CO_2$.

Figure 16:
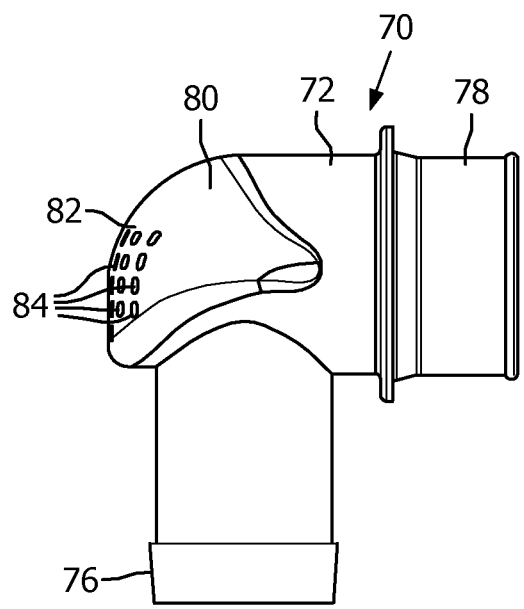
FIG. 16 is a side elevational view.
Figure 17:
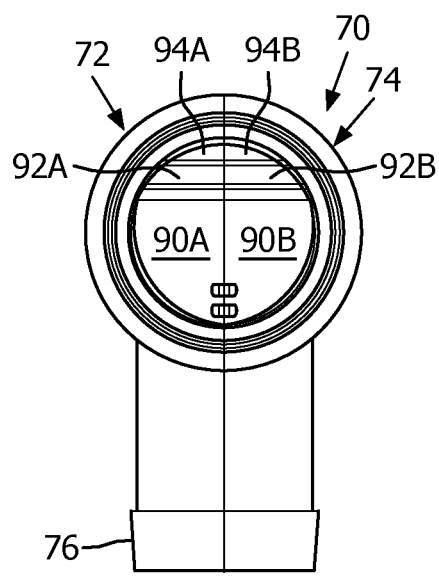
FIG. 17 is a rear elevational view.
Figure 18:
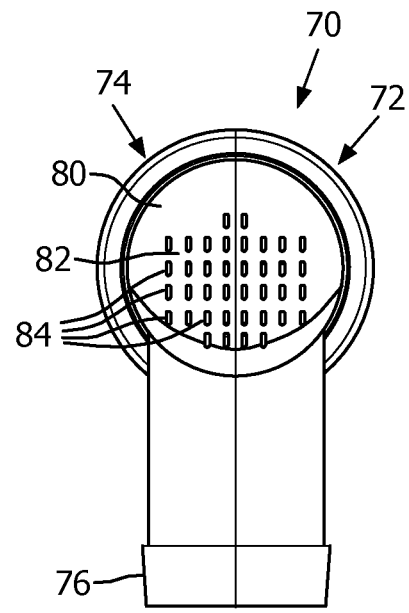
FIG. 18 is a front elevational view of an elbow conduit according to another exemplary embodiment of the present invention.

FIG. 16 is a side elevational view, FIG. 17 is a rear elevational view, and FIG. 18 is a front elevational view of an elbow conduit 70 according to another exemplary embodiment of the present invention. Elbow conduit 70 may be used in conjunction with mask 4 shown in FIG. 1 in place of elbow conduit 6, or in conjunction with any other suitable mask structure. In the exemplary embodiment, elbow conduit 70 comprises a left side portion 72 (FIG. 19) and a right side portion 74 (FIG. 20) that, as described below, are similarly structured and are coupled to one another to form elbow conduit 70.

Figure 19:
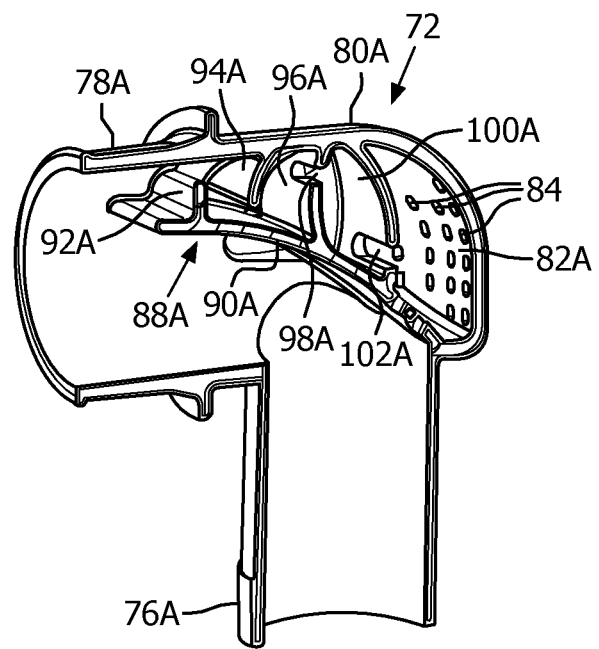
FIG. 19 is an isometric view of a left side portion of the elbow conduit of FIGS. 16-18 and FIG. 20 is an isometric view of a right side portion of the elbow conduit of FIGS. 16-18.
Figure 20:
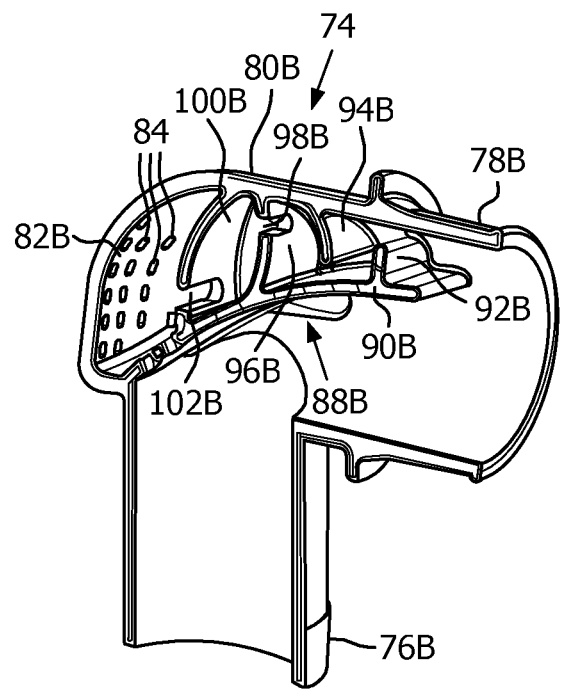

Referring to FIG. 19, left side portion 72 includes an inlet end portion 76A and an outlet end portion 78A, and a middle wall portion 80A located between inlet end portion 76A and outlet end portion 78A. In addition, an outer wall portion 82A of middle wall portion 80A (positioned directly opposite the half opening formed at outlet end portion 78A) includes a plurality of integrally molded oval-shaped exhaust gas slots/orifices 84 extending therethrough. Referring to FIG. 20, right side portion 74 includes inlet end portion 76B and outlet end portion 78B, and middle wall portion 80B located between inlet end portion 76B and outlet end portion 78B. In addition, outer wall portion 82B of middle wall portion 80B (positioned directly opposite the half opening formed at outlet end portion 78B) includes a plurality of integrally molded oval-shaped exhaust gas slots/orifices 84 extending therethrough.

Thus, when left side portion 72 and right side portion 74 are coupled to one another as shown in FIGS. 16-18, inlet end portions 76A, 76B come together to form inlet end portion 76, outlet end portions 78A, 78B come together to form outlet end portion 78, middle wall portions 80A, 80B come together to form central chamber portion 80 having outer wall 82 formed by outer wall portions 82A, 82B. Exhaust gas slots/orifices 84 allow for the dissipation of $CO_2$ to atmosphere as the patient exhales into a mask, such as mask 4, to which elbow conduit 70 is coupled. In addition, exhaust gas slots/orifices 84 act as sound wave diffractors on the exhaust gas flow in order to reduce the noise caused by the exhaust gas flow. In one particular, non-limiting exemplary embodiment, the diameter of each of the oval-shaped exhaust gas slots/orifices 84 is 0.020 inches and the length of each of the oval-shaped exhaust gas slots/orifices 84 is 0.042 inches.

In addition, a partitioning structure 88A is provided as part of left side portion 72 and extends from middle wall portion 80A. Partitioning structure 88A includes an arc-shaped bottom wall 90A having a distal end located near the top of outlet end portion 78A, a first partial wall 92A extending upwardly from bottom wall 90A but not reaching the top of middle wall portion 80A, a second partial wall 94A extending downwardly from the top of middle wall portion 80A but not reaching bottom wall 90A, a third wall 96A extending between the top of middle wall portion 80A and bottom wall 90A and having notch 98A provided therein, and a fourth wall 100A extending between the top of middle wall portion 80A and bottom wall 90A and having notch 102A provided therein. Fourth wall 100A is spaced from outer wall portion 82A. Similarly, partitioning structure 88B is provided as part of right side portion 74 and extends from middle wall portion 80B. Partitioning structure 88B includes an arc-shaped bottom wall 90B having a distal end located near the top of outlet end portion 78B, a first partial wall 92B extending upwardly from bottom wall 90B but not reaching the top of middle wall portion 80B, a second partial wall 94B extending downwardly from the top of middle wall portion 80B but not reaching bottom wall 90B, a third wall 96B extending between the top of middle wall portion 80B and bottom wall 90B and having notch 98B provided therein, and a fourth wall 100B extending between the top of middle wall portion 80B and bottom wall 90B and having notch 102B provided therein. Fourth wall 100B is spaced from outer wall portion 82B.

When left side portion 72 and right side portion 74 are coupled to one another as shown in FIGS. 16-18, partitioning structure 88A and partitioning structure 88B come together to form multiple sound chambers through which the exhaust gas flow, including the patient exhalation, may pass. A first sound chamber is formed between first partial walls 92A, 92B and second partial walls 94A, 94B (flow is over first partial walls 92A, 92B and under second partial walls 94A, 94B), a second sound chamber is formed between second partial walls 94A, 94B and third walls 96A, 96B (flow is through notches 98A, 98B), and a third sound chamber is formed between third walls 96A, 96B and fourth walls 100A, 100B (flow is through notches 102A, 102B). The multiple sound chambers reflect and diffuse the sound pressure wave associated with the exhaust gas flow in a manner wherein a low noise threshold may be achieved while maintaining acceptable flow levels to adequately expel $CO_2$. Positive pressure breathing gas is delivered to the patient through elbow conduit 70 and flows from inlet end 76 to outlet end 78 below arc-shaped bottom walls 90A, 90B.

In the exemplary embodiment, as seen in FIGS. 19 and 20, the outer edges of left side portion 72 are recessed and are structured to receive the raised outer edges of right side portion 74 in order to couple left side portion 72 to right side portion 74.

Figure 21:
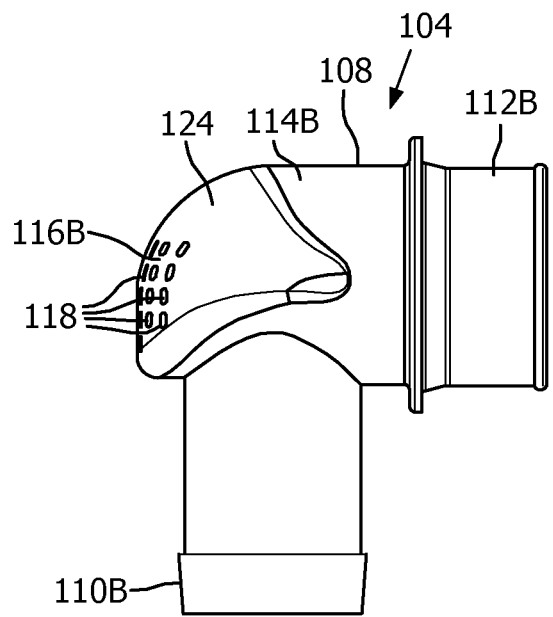
FIG. 21 is a side elevational view.
Figure 22:
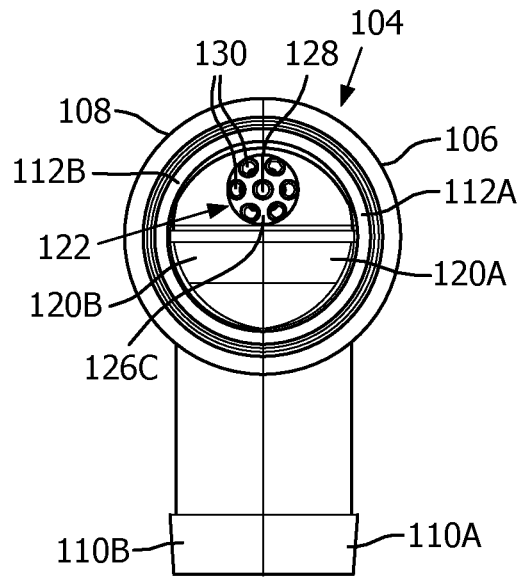
FIG. 22 is a rear elevational view.
Figure 23:
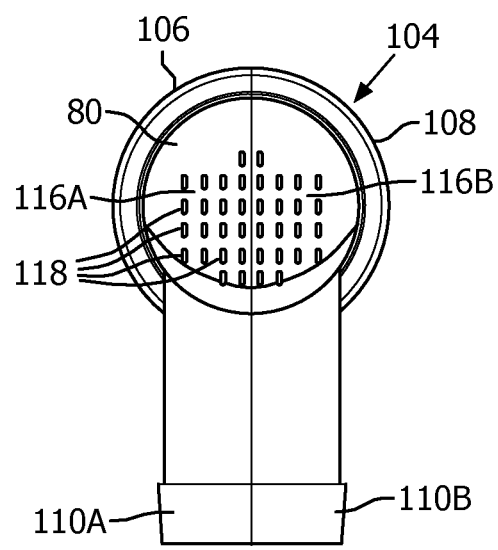
FIG. 23 is a front elevational view of an elbow conduit according to still another exemplary embodiment of the present invention.

FIG. 21 is a side elevational view, FIG. 22 is a rear elevational view, and FIG. 23 is a front elevational view of an elbow conduit 104 according to yet another exemplary embodiment of the present invention. Elbow conduit 104 may be used in conjunction with mask 4 shown in FIG. 1 in place of elbow conduit 6, or in conjunction with any other suitable mask structure. In the exemplary embodiment, elbow conduit 104 comprises right side portion 106 (FIGS. 24-26) and left side portion 108 that, as described below, are similarly structured and are coupled to one another to form elbow conduit 104.

Figure 24:
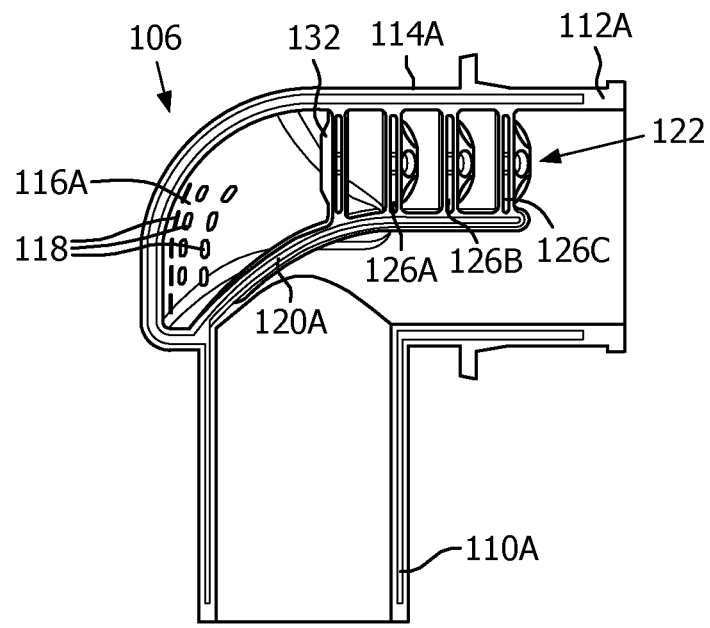
FIGS. 24-26 are isometric views of a right side portion of the elbow conduit of FIGS. 21-23.
Figure 25:
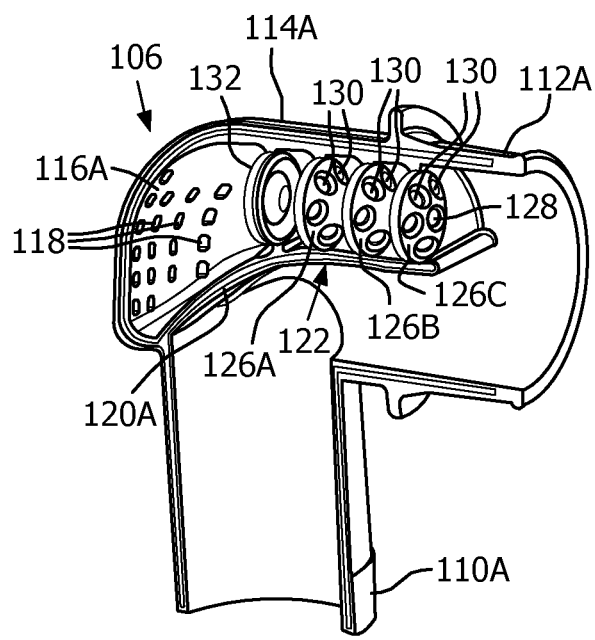
Figure 26:
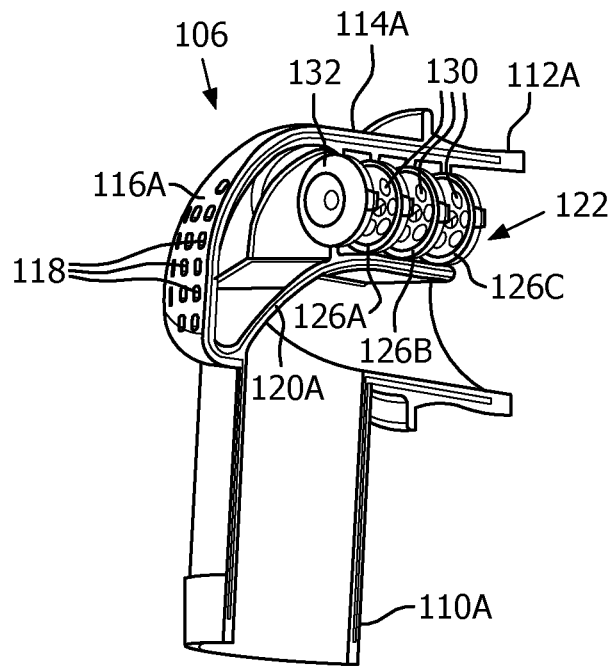

Referring to FIGS. 24-26, right side portion 106 includes an inlet end portion 110A and an outlet end portion 112A, and a middle wall portion 114A located between inlet end portion 110A and outlet end portion 112A. In addition, outer wall portion 116A of middle wall portion 114A (positioned directly opposite the half opening formed at outlet end portion 112A) includes a plurality of integrally molded oval-shaped exhaust gas slots/orifices 118 extending therethrough. Right side portion 106 also includes an arc-shaped bottom wall 120A having a distal end located near the top of outlet end portion 112A. Right side portion 106 supports a silencer assembly 122, described in greater detail below, between bottom wall 120A and the top of middle wall portion 114A. Left side portion 108 is similar in structure to right side portion 106. Left side portion 108 thus includes an inlet end portion 110B, an outlet end portion 112B, a middle wall portion 114B, an outer wall portion 116B, an oval-shaped exhaust gas slots/orifices 118, and an arc-shaped bottom wall 120B.

Thus, when right side portion 106 and left side portion 108 are coupled to one another as shown in FIGS. 21-23, inlet end portions 110A, 110B come together to form inlet end portion 110, outlet end portions 112A, 112B come together to form outlet end portion 112, middle wall portions 114A, 114B come together to form central chamber portion 124 having outer wall 116 formed by outer wall portions 116A, 116B. Exhaust gas slots/orifices 118 allow for the proper dissipation of $CO_2$ to atmosphere as the patient exhales into a mask, such as mask 4, to which elbow conduit 104 is coupled. In addition, exhaust gas slots/orifices 118 act as sound wave diffractors on the exhaust gas flow in order to reduce the noise caused by the exhaust gas flow. In one particular, non-limiting exemplary embodiment, the diameter of each of the oval-shaped exhaust gas slots/orifices 118 is 0.020 inches and the length of each of the oval-shaped exhaust gas slots/orifices 118 is 0.042 inches.

In addition, as noted above, silencer assembly 122 is provided within central chamber portion 124. In the embodiment shown in FIGS. 21-26, silencer assembly 122 is in the form of a quasi-parabolic disc array which substantially evenly diffuses the pressure wave associated with the exhaust gas flow rearward for pressure wave cancellation. In particular, silencer assembly 122 includes longitudinally aligned semispherical baffle members 126A, 126B, 126C, each having a central hole 128 and holes 130 located near its edge, i.e., located in the peripheral region of the semispherical baffle member 126 (FIG. 22). Silencer assembly 122 also includes a flange member 132 that is longitudinally aligned semispherical baffle members 126A, 126B, 126C adjacent exhaust gas slots/orifices 118. Flange baffle member 132 includes a central truncated conical portion with an opening at the apex i.e., at the plane of truncation of the conical portion facing towards the baffle members 126A, 126B, 126C and towards the opening formed by outlet end portion 112.

In operation, the exhaust gas flow and associated sound waves are forced through holes 128, 130 in baffle member 126C where they are reflected/deflected and pass on through holes 128, 130 in baffle member 126B where further reflection/deflection causes them to pass through holes 128, 130 in baffling member 126A. The exhaust gas flow and associated sound waves then pass through the central hole of flange baffle member 132 and out through exhaust gas slots/orifices 118. Due to the delay of the passage of the exhaust gas flow and sound waves through the holes 130 of baffle members 126A, 126B, 126C, they are out of phase with the gases and sound waves passing directly through the central holes 128 of baffle members 126A, 126B, 126C. At each semispherical baffle member 126A, 126B, 126C, they tend to cancel and when they meet after they pass through flange baffle member 132, a reduction in noise is achieved. Positive pressure breathing gas is delivered to the patient through elbow conduit 104 and flows from inlet end 110 to outlet end 112 below arc-shaped bottom walls 120A, 120B.

Thus, exhaust gas slots/orifices 118 and silencer assembly 122 combine to provide reflection and diffraction to attenuate the sound pressure wave associated with the exhaust gas flow as it passes through elbow conduit 104, which helps reduce the sound pressure wave enough so that a low noise threshold may be achieved while maintaining acceptable flow levels to adequately expel $CO_2$.

Figure 27:
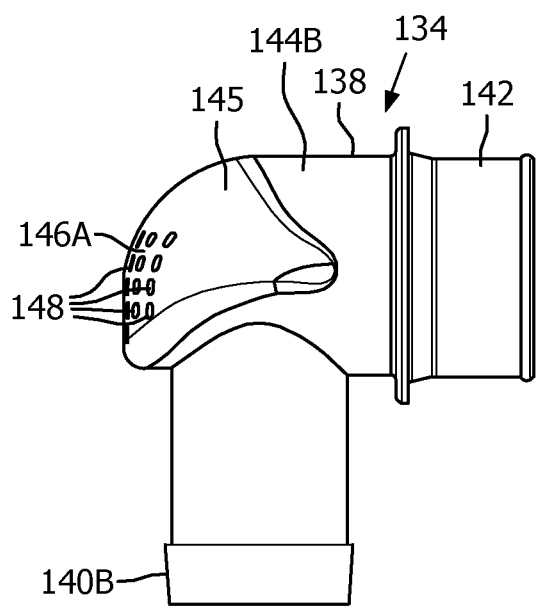
FIG. 27 is a side elevational view.
Figure 28:
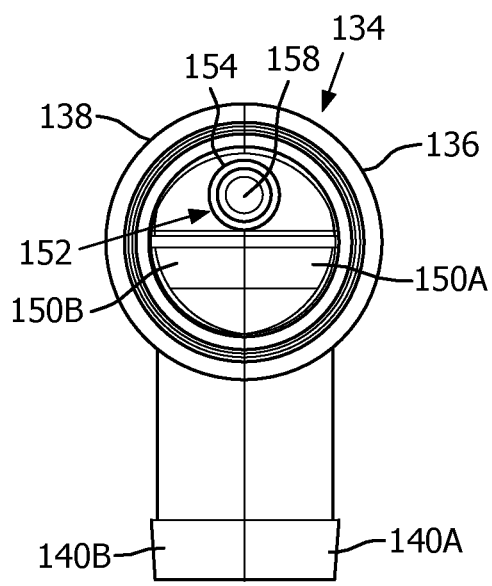
FIG. 28 is a rear elevational view.
Figure 29:
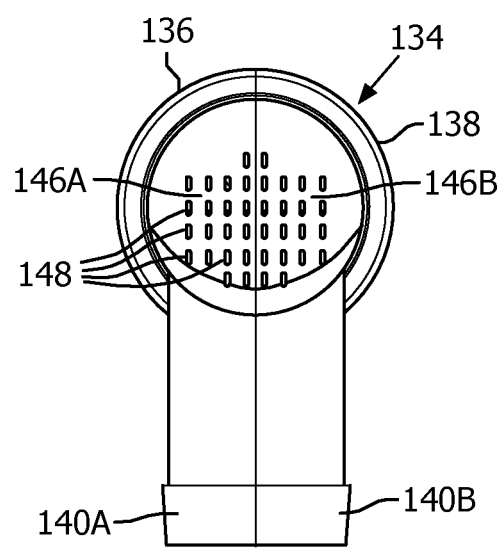
FIG. 29 is a front elevational view of an elbow conduit according to yet another exemplary embodiment of the present invention.

FIG. 27 is a side elevational view, FIG. 28 is a rear elevational view, and FIG. 29 is a front elevational view of an elbow conduit 134 according to still another exemplary embodiment of the present invention. Elbow conduit 134 may be used in conjunction with mask 4 shown in FIG. 1 in place of elbow conduit 6, or in conjunction with any other suitable mask structure. In the exemplary embodiment, elbow conduit 134 comprises a right side portion 136 (FIGS. 30-32) and a left side portion 138 that, as described below, are similarly structured and are coupled to one another to form elbow conduit 134.

Figure 30:
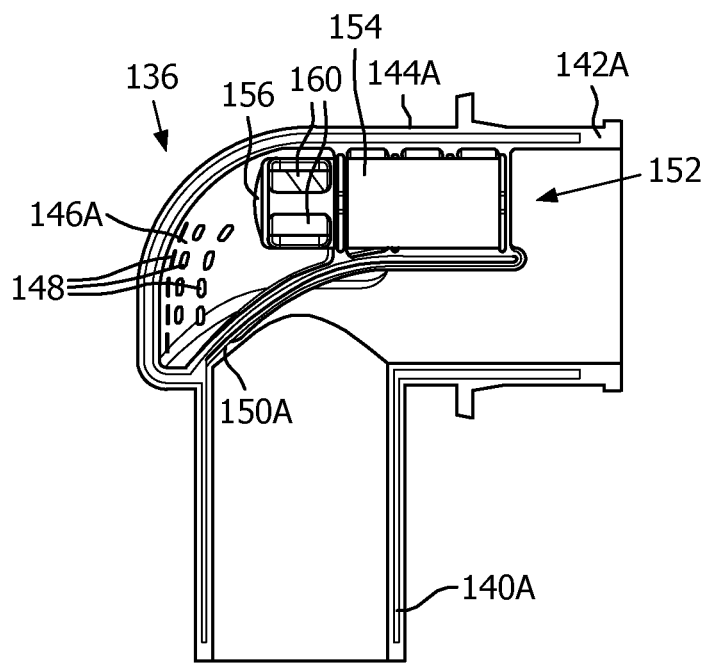
FIGS. 30-32 are isometric views of a right side portion of the elbow conduit of FIGS. 27-29.
Figure 31:
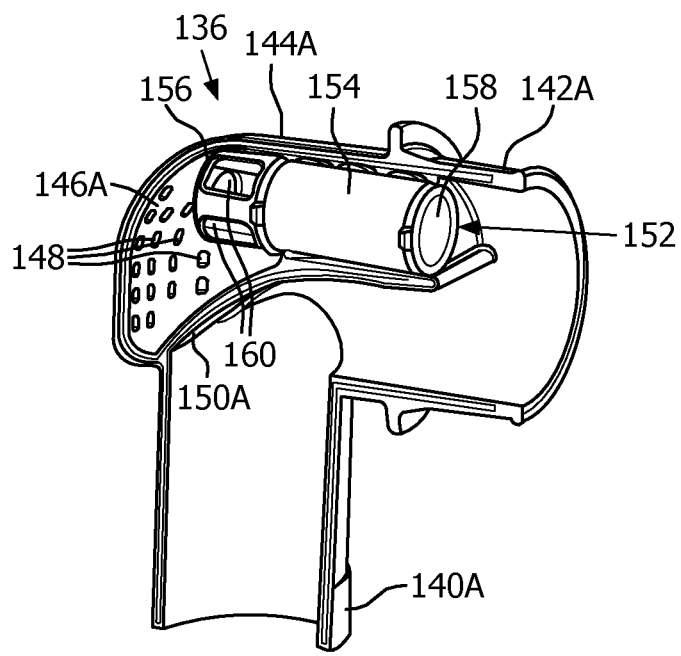
Figure 32:
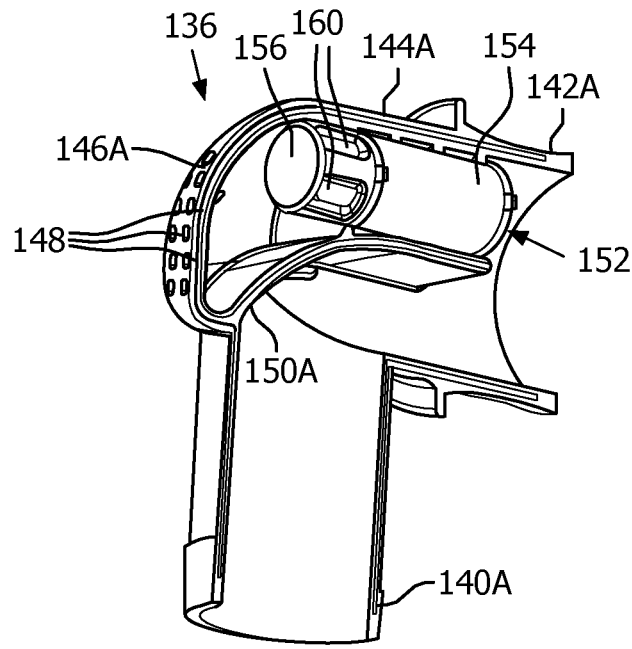

Referring to FIGS. 30-32, right side portion 136 includes inlet end portion 140A and outlet end portion 142A, and middle wall portion 144A located between inlet end portion 140A and outlet end portion 142A. In addition, outer wall portion 146A of middle wall portion 144A (positioned directly opposite the half opening formed at outlet end portion 142A) includes a plurality of integrally molded oval-shaped exhaust gas slots/orifices 148 extending therethrough. Right side portion 136 also includes arc-shaped bottom wall 150A having a distal end located near the top of outlet end portion 142A. Right side portion 136 supports silencer assembly 152, described in greater detail below, between bottom wall 150A and the top of middle wall portion 144A. Left side portion 138 is similar in structure to right side portion 136. Left side portion 138 thus includes inlet end portion 140B, outlet end portion 142B, middle wall portion 144B, outer wall portion 146B, oval-shaped exhaust gas slots/orifices 148, and arc-shaped bottom wall 150B.

Thus, when right side portion 136 and left side portion 138 are coupled to one another as shown in FIGS. 27-29, inlet end portions 140A, 140B come together to form inlet end portion 140, outlet end portions 142A, 142B come together to form outlet end portion 142, middle wall portions 144A, 144B come together to form central chamber portion 155 having outer wall 156 formed by outer wall portions 156A, 156B. Exhaust gas slots/orifices 148 allow for the proper dissipation of $CO_2$ to atmosphere as the patient exhales into a mask, such as mask 4, to which elbow conduit 104 is coupled. In addition, exhaust gas slots/orifices 148 act as sound wave diffractors on the exhaust gas flow in order to reduce the noise caused by the exhaust gas flow. In one particular, non-limiting exemplary embodiment, the diameter of each of the oval-shaped exhaust gas slots/orifices 118 is 0.020 inches and the length of each of the oval-shaped exhaust gas slots/orifices 118 is 0.042 inches.

In addition, as noted above, silencer assembly 152 is provided within central chamber portion 145. In the embodiment shown in FIGS. 27-32, silencer assembly 152 is in the form of a valve assembly within a baffle arrangement to reflect the sound pressure wave associated with exhaust gas flow for noise attenuation. In particular, silencer assembly 152 includes cylindrical hollow body 154 having an inlet opening 158 coupled to outlet member 156 having a plurality of openings 160.

Figure 33:
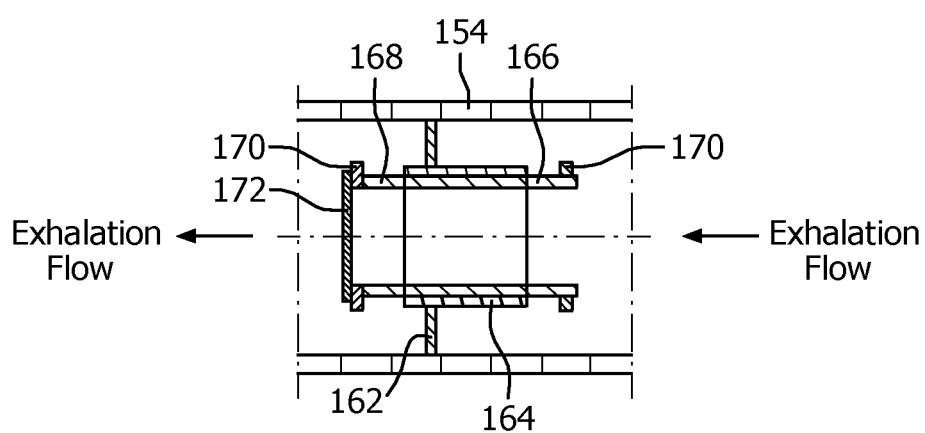
FIG. 33 is a schematic diagram of a portion of the silencer assembly of the elbow conduit of FIGS. 27-29.

Referring to FIG. 33, inner surface of the hollow body 154 includes a baffle ring 162 having an outer circumference that is attached to the hollow body 154 along an inner circumference of hollow body 154. A baffle tube 164 is attached to baffle ring 162 along an inner circumference of baffle ring 162. Baffle tube 164 and hollow body 154 are both substantially cylindrical and are oriented about substantially the same center axis. Piston assembly 166 is moveably provided within baffle tube 164 and includes hollow piston tube 168 having stop rings 170 provided at opposite ends thereof, with a forward end having end cap 172 attached thereto. In addition, the forward end of piston tube 168 includes a number of orifices therein for allowing radial fluid flow out of piston tube 168 when it is pushed outside of baffle tube 164 by the force of the exhaust gas flow (the "open position").

In order to attenuate sound, exhaust gas flow entering silencer assembly 152 is reflected off baffle ring 162 inside hollow body 154. Baffle ring 162 includes a surface substantially perpendicular to the flow of fluid through silencer assembly 152. When exhaust gas flow is reflected off baffle ring 162, at least some noise attenuation is achieved. Exhaust gas flow passing through the piston assembly 166 may reflect off piston cap 172 and outlet member 156 before exiting silencer assembly 152. The reflection off piston cap 172 and outlet member 156 may provide additional noise attenuation. Positive pressure breathing gas is delivered to the patient through elbow conduit 134 and flows from inlet end 140 to outlet end 142 below arc-shaped bottom walls 150A, 150B.

In an alternative embodiment, hollow body 154 may be omitted, and instead baffle ring 162, baffle tube 164 and piston assembly 166 as described above may be provided directly within central chamber portion 145 as a silencer assembly.

Thus, exhaust gas slots/orifices 148 and silencer assembly 152 combine to provide reflection and diffraction to attenuate the sound pressure wave associated with the exhaust gas flow as it passes through elbow conduit 134, which helps reduce the sound pressure wave enough so that a low noise threshold may be achieved while maintaining acceptable flow levels to adequately expel $CO_2$.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface device, comprising:
   (a) a cushion;
   (b) a frame, the cushion being coupled to the frame, the frame having an orifice in fluid communication with the cushion; and
   (c) a fluid coupling conduit comprising:
      an inlet end,
      an outlet end fluidly coupled to the inlet end, wherein the inlet end is structured to receive a flow of breathing gas, wherein the outlet end is structured to be fluidly coupled to the orifice of the frame,
      a central chamber portion positioned between the inlet end and the outlet end, the central chamber portion having an outer wall structured to be positioned opposite the orifice of the frame when the outlet end is fluidly coupled to the orifice,
      a plurality of exhaust gas orifices disposed on the outer wall and extending therethrough, and
      a number of sound attenuating structures disposed in the central chamber portion between the outlet end and the outer wall, the sound attenuating structures including a plurality of surfaces structured to reflect sound waves associated with exhaust gas flow through the orifice of the frame.

2. The patient interface device according to claim 1, wherein the exhaust gas orifices are oval-shaped.

3. The patient interface device according to claim 2, wherein a diameter of each of the oval-shaped exhaust gas orifices is 0.020 inches and a length of each of the oval-shaped exhaust gas orifices is 0.042 inches.

4. The patient interface device according to claim 1, wherein the sound attenuating structures comprises a plurality of partition members coupled and extending from an interior surface of the outer wall.

5. The patient interface device according to claim 4, wherein each partition member includes a leading edge region having a plurality of arc-shaped portions.

6. The patient interface device according to claim 5, wherein each partition member includes a first arc-shaped portion, a second arc-shaped portion, and a third arc-shaped portion, wherein second arc-shaped portion positioned between the first arc-shaped portion and the third arc-shaped portion and is configured as a parabolic notched region.

7. The patient interface device according to claim 1, wherein the fluid coupling conduit includes a plurality of arc shaped deflector members extending outwardly from an exterior of the outer wall at a downward angle with respect to a plane that is parallel to the outer wall.

8. The patient interface device according to claim 1, wherein the sound attenuating structures comprises a plurality of reflecting structures, each reflecting structure being coupled to and extending from an interior surface of the central chamber portion and including a plurality of exterior surfaces that are positioned at an angle with respect to one another.

9. The patient interface device according to claim 1, wherein the number of sound attenuating structures comprises a partitioning structure having a plurality of walls, wherein the plurality of walls form a plurality of sound chambers through which the exhaust gas flow may pass, wherein the plurality of sound chambers reflect and diffuse the sound waves associated with the exhaust gas flow.

10. The patient interface device according to claim 1, wherein the sound attenuating structures comprises a noise silencer assembly, the noise silencer assembly including a plurality of longitudinally aligned semispherical baffle members, each baffle member having a plurality of holes for passing the exhaust gas flow.

11. The patient interface device according to claim 10, wherein in each baffle member, the holes comprise a central hole and a plurality of peripheral holes located in a peripheral region of the baffle member.

12. The patient interface device according to claim 10, wherein the noise silencer assembly is supported by an arc-shaped bottom wall provided in the central chamber portion, the arc-shaped bottom wall having a distal end located adjacent a top of the outlet end portion, and wherein the flow of breathing gas flows from the inlet end to the outlet end below the arc-shaped bottom wall.

13. The patient interface device according to claim 1, wherein the number of sound attenuating structures comprises a noise silencer assembly, the noise silencer assembly including a hollow body housing a valve assembly supported within a baffle assembly.

14. The patient interface device according to claim 1, wherein the fluid coupling conduit is an elbow conduit.

* * * * *